United States Patent [19]

Renner et al.

[11] Patent Number: 4,709,047
[45] Date of Patent: Nov. 24, 1987

[54] SUBSTITUTED UNSATURATED, SULFONYLOXY GROUP-CONTAINING BICYCLIC IMIDES AS CATALYSTS FOR CATIONIC POLYMERIZATION

[75] Inventors: Alfred Renner, Muntelier; Christian Vonlanthen, Lentigny, both of Switzerland

[73] Assignee: Ciba-Geigy Corporation, Ardsley, N.Y.

[21] Appl. No.: 819,656

[22] Filed: Jan. 17, 1986

[30] Foreign Application Priority Data

Jan. 29, 1985 [CH] Switzerland ............................ 388/85

[51] Int. Cl.$^4$ ............................................ C07D 209/94
[52] U.S. Cl. .................................... 548/435; 526/259; 526/262
[58] Field of Search .......................................... 548/435

[56] References Cited

U.S. PATENT DOCUMENTS

| | | | |
|---|---|---|---|
| 3,105,839 | 10/1963 | Renner | 549/237 |
| 3,450,711 | 6/1969 | Megna et al. | 548/435 |
| 4,513,003 | 4/1985 | Kuhle et al. | 548/435 |
| 4,515,962 | 5/1985 | Renner | 548/435 |
| 4,604,437 | 8/1986 | Renner | 548/435 |

FOREIGN PATENT DOCUMENTS

| | | | |
|---|---|---|---|
| 166693 | 6/1985 | European Pat. Off. | 548/435 |
| 943050 | 5/1956 | Fed. Rep. of Germany | 548/435 |

Primary Examiner—Mary E. Ceperley
Attorney, Agent, or Firm—Luther A. R. Hall

[57] ABSTRACT

Imides of formula I

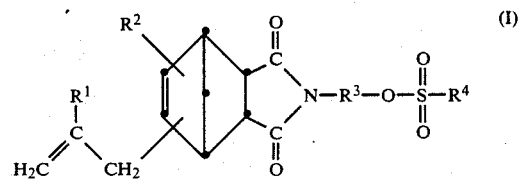

wherein $R^1$ and $R^2$ are independently hydrogen or methyl, $R^3$ is a direct bond, alkylene, oxaalkylene, cycloalkylene, arylene or arylene-T-arylene where T is methylene or isopropylidene, and $R^4$ alkyl, cycloalkyl, aryl, benzyl or alkaryl are suitable as catalysts for the crosslinking of specific unsaturated imides.

9 Claims, No Drawings

SUBSTITUTED UNSATURATED, SULFONYLOXY GROUP-CONTAINING BICYCLIC IMIDES AS CATALYSTS FOR CATIONIC POLYMERIZATION

The invention relates to sulfonyloxy group-containing bicyclo[2.2.1]hept-5-ene-2,3-dicarboxylic acid imides which are substituted by allyl or methallyl and may additionally be substituted by methyl, to the preparation of said imides and to the use thereof as catalysts for the cationic polymerisation of specific unsaturated imides. U.S. Pat. No. 3,450,711 describes bisimide compounds which are prepared by reacting endo,cis-bicyclo[2.2.1-]hept-5-ene-2,3-dicarboxylic acid anhydride (=5-norbornene-2,3-dicarboxylic acid anhydride) with selected organic diamines. Said bisimides contain no methyl, methallyl or allyl substituents in the imide group and differ from the compounds of the present invention both with respect to their structure and with respect to their chemical reactivity. The compounds disclosed in the U.S. patent cited above are employed as intermediates in the preparation of epoxy compounds.

European patent application No. 0 105 024 describes allyl- or methallyl-substituted bicyclo[2.2.1]hept-5-ene-2,3-dicarboxylic acid imides and the polymers obtainable therefrom.

The sulfonyloxy group-containing bicyclo[2.2.1-]hept-5-ene-2,3-dicarboxylic acid imides of the present invention are valuable latent catalysts for the cationic polymerisation of specific unsaturated imides which provides crosslinked polymers of excellent properties. Said imides are of the following formula I:

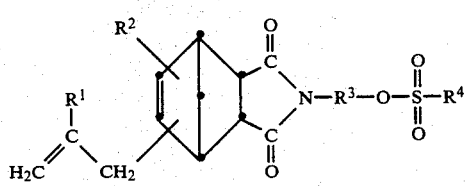
(I)

wherein each of $R^1$ and $R^2$ independently of the other is hydrogen or methyl, $R^3$ is a direct bond, a $C_2$–$C_{20}$ aliphatic radical which may be interrupted in the chain by oxygen atoms, or is a mono- or polynuclear $C_5$–$C_{20}$ cycloaliphatic radical, a $C_6$–$C_{20}$ aromatic radical or a group of formula II

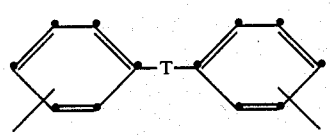
(II)

wherein T is methylene, isopropylidene, CO, O, S or $SO_2$, and $R^4$ is $C_1$–$C_{12}$ alkyl, $C_5$–$C_8$ cycloalkyl, $C_6$–$C_{10}$ aryl, benzyl or $C_7$–$C_{12}$ alkaryl.

Each of $R^1$ and $R^2$ is preferably a hydrogen atom.

$R^3$ may be a divalent straight chain or branched aliphatic radical containing 2 to 20, preferably 2 to 12 and most preferably 2 to 6, carbon atoms which is optionally interrupted in the chain by one or more oxygen atoms. Examples of suitable aliphatic radicals $R^3$ are ethylene, 1,2- and 1,3-propylene, butylene, pentamethylene, hexamethylene, heptylene, octylene, decylene, dodecylene, hexadecylene and neopentylene. Aliphatic radicals interrupted by oxygen atoms may be derived for example from ethylene glycol or propylene glycol and may correspond to groups of the formula

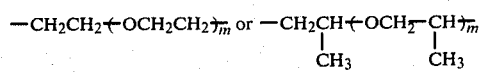

in which formulae m is 1 to 8.

$R^3$ may also be a mono- or polynuclear cycloaliphatic divalent radical containing 5 to 20 carbon atoms, e.g. cyclopentylene, cyclohexylene, cycloheptylene, cyclooctylene, bis(cyclohexylene)-methane, 2,2-bis(cyclohexylene)propane and decalinylene.

$R^3$ as an aromatic radical is preferably a 1,3- or 1,4-phenylene or naphthylene, each of which, if desired, may be substituted by one or more $C_1$–$C_4$ alkyl groups such as methyl, ethyl or propyl. Said groups are preferably unsubstituted. 1,3- and 1,4-phenylene groups are particularly preferred aromatic radicals.

If $R^3$ is a group of formula II, then T is preferably O, $SO_2$ or, most preferably, methylene or isopropylidene.

Particularly preferred compounds of formula I are those wherein $R_3$ is a direct bond, a $C_2$–$C_{10}$ aliphatic radical or a —$CH_2CH_2$—$OCH_2CH_2$—$_m$ group, wherein m is 1 or 2, a $C_5$–$C_6$-cycloaliphatic or a $C_6$–$C_{10}$ aromatic radical or a group of formula II, wherein T is methylene or isopropylidene.

$R^4$ may be a branched or, preferably, straight chain alkyl group containing 1 to 12, preferably 1 to 6 and most preferably 1 or 2, carbon atoms. Examples of suitable alkyl groups are dodecyl, decyl, octyl, heptyl, butyl, propyl and, most preferably, ethyl or methyl.

$R^4$ as a cycloalkyl radical is preferably cyclopentyl or cyclohexyl, each of which may be substituted by one or more $C_1$–$C_3$ alkyl groups. Said cycloalkyl groups are preferably unsubstituted.

$R^4$ as an aryl radical is preferably phenyl or naphthyl. Examples of suitable $C_7$–$C_{12}$ alkaryl groups are phenyl or naphthyl, each substituted by one or more $C_1$–$C_3$ alkyl groups. The preferred meaning of $R^4$ as aryl is tolyl.

Particularly preferred compounds of formula I are those wherein $R^4$ is $C_1$–$C_6$ alkyl, $C_5$–$C_6$ cycloalkyl, $C_6$–$C_{10}$ aryl or $C_7$–$C_{12}$ aralkyl.

More particularly preferred compounds of formula I are those wherein $R^3$ is a direct bond or the radical —$CH_2CH_2$—,

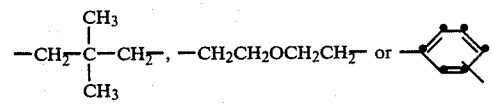

and $R^4$ is methyl, phenyl, 2-naphthyl or p-tolyl.

The most preferred compound of formula I is that wherein each of $R^1$ and $R^2$ is hydrogen, $R^3$ is a direct bond or the radical —$CH_2CH_2$— and $R^4$ is methyl or phenyl.

The imides of the present invention can be prepared in a manner known per se e.g. by reacting an anhydride of formula III

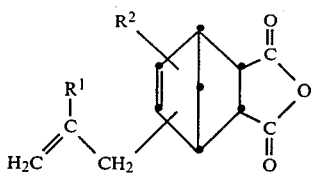

with a compound of formula IV $$H_2N—R^3—OH \quad (IV)$$

at elevated temperature and with removal by distillation of the water forming during the reaction, to give a compound of formula V

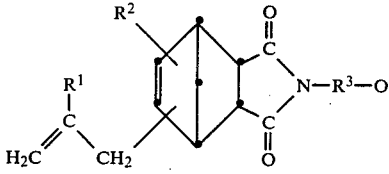

and by subsequently reacting the imide of formula V with a sulfonyl chloride of formula VI $$R^4—SO_2Cl \quad (VI)$$

with cooling and in the presence of an HCl acceptor, preferably an amine such as triethylamine, $R^1$, $R^2$, $R^3$ and $R^4$ being as defined for formula I.

Provided the compounds of formula IV are low boiling amines, it is recommended to employ these reactants in excess. The reaction may be carried out without a solvent or in the presence of an inert solvent which can be employed for the azeotropic removal of the water (entrainer). The temperature of the reaction may be in the range from 100° to 250° C. It is preferred to prepare the imides of formula I in the melt under a pressure of not more than 4500 Pa and at temperatures in the range from 130° to 220° C., preferably from 180° to 220° C.

The starting materials of formula III can be prepared according to the process described in U.S. Pat. No. 3,105,839 by reacting sodium cyclopentadienide or sodium methylcyclopentadienide with an allyl halide or methallyl halide, followed by a Diels-Alder reaction with maleic anhydride. Although it is stated in said U.S. patent specification that the allyl group is bonded in the 7-position of the bicylic system, more recent investigations show that an isomeric mixture with respect to the position of the allyl group (in the 1- and 6-positions) and also with respect to the endo- and exoconfiguration of the anhydride moiety is formed.

Compounds of formula IV are known or can be prepared by methods known per se. This also applies to compounds of formula VI.

The reaction of compounds of formula V with the sulfonyl chlorides of formula VI is preferably carried out using equimolar amounts of the reactants in an inert solvent with a boiling point of below 200° C. Examples of suitable solvents are aliphatic or alicyclic, optionally chlorinated, hydrocarbons and, in particular, aromatic, optionally chlorinated, hydrocarbons such as chlorobenzene, xylene and, in particular, toluene. In order to neutralise the hydrochloric acid forming during the reaction, it is carried out in the presence of an HCl acceptor, preferably a tertiary amine such as triethylamine, dimethylaniline, pyridine or lutidine. Since the reaction is exothermic, it is carried out with cooling so that the temperature of the reaction mixture does not exceed, preferably, 10° C.

The compounds of the invention are liquid or low melting solid substances. At elevated temperature the sulfonyloxy group-containing imides of the present invention generate the corresponding sulfonic acid $R^4SO_3H$, wherein $R^4$ is as defined for formula I, and are therefore suitable as latent catalysts for the crosslinking of specific cationically polymerisable unsaturated imides. On account of its polyfuntionality, the residue remaining after removal of the sulfonic acid is incorporated into the final polymer. A mixture of several of the above-described compounds of formula I of the present invention may also be employed as catalyst.

The present invention also relates to curable mixtures containing (a) one or more imides of formula I and (b) an alkenylbicyclo[2.2.1]hept-5-ene-2,3-dicarboxylic acid imide.

Examples of alkenylbicyclo[2.2.1]hept-5-ene-2,3-dicarboxylic acid imides suitable for the curable compositions of the present invention are those which are described in European patent application No. 105 024. Said imides may be employed by themselves or as mixtures of at least two components.

The most preferred alkenylbicyclo[2.2.1]hept-5-ene-2,3-dicarboxylic acid imides of the present invention are the above-mentioned substituted bicyclo[2.2.1]hept-5-ene-2,3-dicarboxylic acid imides according to European patent application No. 0 105 024. They may also additionally contain a methyl group in the bicycloheptene ring.

The concentration of the catalyst of formula I to be employed in accordance with the present invention is conveniently in the range from 0.1 to 15.0, preferably from 0.25 to 5.0 and most preferably from 0.5 to 2.0, % by weight, based on the cationically polymerisable material.

The reaction is preferably carried out in the melt or partly in the melt and partly in the solid phase. It may also be carried out in solution. In most cases, however, the addition of solvents can be dispensed with since the starting mixtures themselves are liquid or low melting solid substances.

Examples of suitable solvents are aromatic hydrocarbons such as benzene, toluene and xylene, and also tetraline and decaline, as well as chlorinated hydrocarbons such as ethylene chloride and chlorobenzene, and glycol ethers such as the monomethyl, monoethyl, monobutyl and monophenyl ether of ethylene glycol and diethylene glycol.

The process may also be carried out in two steps in the following manner. After mixing and optionally after subsequently grinding all starting products, the powder or liquid is first heated for a limited period preferably to a temperature in the range from 120° to 170° C. A still thermoplastic, partially soluble product is formed. This prepolymer must, if necessary, be reground to a processible powder before it is ultimately cured in the final processing. Prepolymerisation may also be effected by heating a solution or suspension of the starting materials.

The process of the present invention for the preparation of crosslinked polymers is usually carried out with simultaneous moulding to give moulded articles, plenar structures, laminates, bonds or foamed plastics. Adjuvants customarily employed in curable plastics technology, such as fillers, plasticisers, pigments, dyes, mould lubricants and flame retardants, may also be added to the curable substances. Examples of suitable fillers are glass fibres, carbon fibres, micae, graphite, quartz powder, kaolin, colloidal silica or metal powders. Examples of suitable mould lubricants are silicone oil, various waxes, zinc or calcium stearate.

The moulding of the products which can be prepared by the process of the present invention may be carried out by the casting process using a casting mould.

However, moulding may also be carried out by hot pressing using a press. It is usually sufficient to heat briefly to temperatures in the range from 160° to 250° C. under a pressure in the range from 9.81·10⁴ to 1.96·10⁷ Pa, and then to complete the curing of the resultant moulded article outside the press.

By employing the compounds of formula I of the present invention as catalysts for cationic polymerisation, curing is possible at lower temperatures and with considerably shorter cycle times. The resultant products exhibit excellent mechanical and thermal properties.

The following Examples illustrate the preparation of a number of imides of the present invention, as well as the properties and application thereof.

EXAMPLE 1

Allylbicyclo[2.2.1]hept-5-ene-2,3-dicarboxylic acid N-benzenesulfonyloxyimide

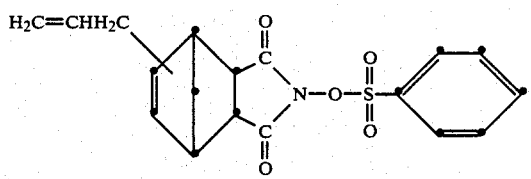

(a)

Allylbicyclo[2.2.1]hept-5-ene-2,3-dicarboxylic acid N-hydroxyimide.

139 g (2 mol) of hydroxylamine hydrochloride are dissolved in 200 ml of water, 408 g (2 mol) of allylbicyclo[2.2.1]hept-5-ene-2,3-dicarboxylic acid anhydride (prepared according to Example 1 of U.S. Pat. No. 3,105,839) are added to the solution and, with vigorous stirring, 160 g of 50% aqueous NaOH solution are then added dropwise. The mixture is subsequently heated for 1 hour under reflux, the water and traces of oily components are distilled off and the residue is taken up in toluene. The toluene phase is filtered in order to remove the sodium chloride, and the toluene is subsequently removed by rotary evaporation at 150° C. and 2000 Pa, affording 402.6 g of the product (91.5% of theory) as a pale brown viscous liquid with a viscosity of 1.28 Pa.s at 80° C.

| Analysis: | calc. for $C_{22}H_{13}NO_3$ | found |
|---|---|---|
| % C: | 65.74 | 65.34 |
| % H: | 5.98 | 6.02 |
| % H: | 6.39 | 6.40 |

(b)

The product obtained according to step (a) is dissolved in 1 liter of toluene, and 222.8 g of triethylamine are added to the solution. The mixture is stirred until a homogeneous solution is obtained and this solution is then cooled to 0° C. With vigorous stirring and with external cooling, 324.7 g of benzenesulfonyl chloride are added dropwise such that the temperature of the reaction mixture is held in the range from 5° to 10° C. The mixture is stirred overnight at room temperature, water is added, the pH is adjusted with concentrated HCl to 5 and the mixture is washed twice more with water (75° C.). After separation of the aqueous phase, the organic phase is dried over Na₂SO₄ and filtered and the filtrate is concentrated by rotary evaporation at 110° C. and 2000 Pa, affording 471 g of a viscous liquid which crystallises on standing (m.p. 97°–99° C.).

| Elementary analysis: | calc. for $C_{18}H_{17}NO_5S$ | found |
|---|---|---|
| % C: | 60.16 | 60.35 |
| % H: | 4.77 | 4.85 |
| % N: | 3.90 | 3.90 |
| % S: | 8.92 | 8.59 |

IR spectrum (cm⁻¹): 575.4, 685.5 and 736.2 aryl; 1195 and 1398 —SO₂—O—; 1620 cyclic double bond; 1640 allyl double bond; 1742 carbonyl.

EXAMPLE 2

Methallylmethylbicyclo[2.2.1]hept-5-ene-2,3-dicarboxylic acid N-benzenesulfonyloxyimide 58 g of methallylmethylbicyclo[2.2.1]hept-5-ene-2,3-dicarboxylic acid anhydride (b.p.=117°–120° C. at 2.7 Pa; $n_{25}{}^D n^D{}_{25}$=1.5071) (prepared by a procedure analogous to those of Examples 1 and 2 of U.S. Pat. No. 3,105,839)
17.35 g of hydroxylamine hydrochloride
20.78 g of aqueous NaOH (48.11% by weight)
50 g of H₂O and
100 g of toluene
are reacted as described in Example 1a, affording 54.95 g of a mixture of isomers of methallylmethylbicylo[2.2.1]hept-5-ene-2,3-dicarboxylic acid N-hydroxylimide. According to gas chromatography, said mixture consists of 12 isomers.

24.7 g of this product and 11.13 g of triethylamine are dissolved in 80 g of toluene. This solution is reacted at 7°–8° C. with 17.66 g of benzoylsulfonyl chloride and the mixture is allowed to continue reacting overnight. 80 ml of water are added and the pH is adjusted with HCl to 5. The reaction mixture is washed twice with water, dried over Na₂SO₄ and filtered and the filtrate is concentrated by rotary evaporation, affording 34.2 g (87.8% of theory) of a clear, reddish brown resin with a viscosity of 1.96 Pa.s.

| Elementary analysis: | calc. for $C_{20}H_{21}NO_5S$ | found |
|---|---|---|
| % C: | 62.00 | 62.14 |
| % H: | 5.46 | 5.60 |
| % N: | 3.62 | 3.60 |
| % S: | 8.27 | 7.95 |

IR spectrum (cm$^{-1}$): 575.4, 685.8 and 738.2. aryl; 1195.5 and 1397 —SO$_2$—O—; 1620 cyclic double bond; 1640 allyl double bond; 1742 carbonyl.

EXAMPLE 3

Allylbicyclo[2.2.1]hept-5-ene-2,3-dicarboxylic acid N-(2'-benzenesulfonyloxyethyl)imide

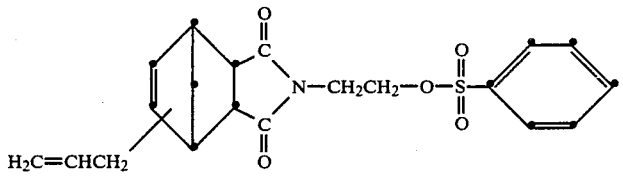

(a)

Allylbicyclo[2.2.1]hept-5-ene-2,3-dicarboxcylic acid N-(2'-hydroxyethyl)imide

A reaction vessel is charged with 760 g of allylbicyclo[2.2.1]hept-5-ene-2,3-dicarboxylic acid anhydride and, with stirring, 227.55 g of monoethanolamine are added dropwise. The mixture is heated under reflux for 2 hours and then water and a small amount of excess monoethanolamine are distilled off until a temperature of 175° C. has been reached. The pressure is then lowered to 2670 Pa. The mixture is cooled to 100° C. and the product is rectified at 4.9 Pa. 712.4 g (77.3 % of theory) of a pale yellow oil with the following data distill at a temperature in the range from 170° to 174° C.: $n_{25}^D$ $n^D{}_{25} = 1.5344$.

$\eta_{25} = 2.43$ Pa.s.

| Analysis: | calc. | found |
|---|---|---|
| % C: | 68.00 | 68.08 |
| % H: | 6.93 | 7.06 |
| % N: | 5.66 | 5.61 |

IR spectrum (cm$^{-1}$): 1619 cyclic double bond; 1641 allyl group; 1697 carbonyl group; 1768 carbonyl in the cyclic imide; 3449 hydroxyl group.

(b)

123 g of the product obtained according to step (a)
55.55 g of triethylamine
400 g of toluene and
88.31 g of benzoylsulfonyl chloride
are reacted as described in the foregoing Examples, affording 171.25 g (88.5% of theory) of a reddish brown, clear resin with a viscosity of 0.426 Pa.s at 80° C.

| Elementary analysis: | calc. for C$_{20}$H$_{21}$NO$_5$S | found |
|---|---|---|
| % C: | 62.00 | 62.29 |
| % H: | 5.46 | 5.56 |
| % N: | 3.62 | 3.48 |
| % S: | 8.27 | 8.13 |

EXAMPLE 4

Allylbicyclo[2.2.1]hept-5-ene-2,3-dicarboxylic acid N-methanesulfonyloxyimide 43.8 g of the product prepared according to Example 1a
22.2 g of triethylamine
160 g of toluene and
22.91 g of methanesulfonyl chloride
are reacted in accordance with the procedure described in Example 1b, affording 46.9 g (79% of theory) of a dark brown resin;
$\eta_{80} = 0.31$ Pa.s.

| Elementary analysis: | calc. for C$_{13}$H$_{15}$NO$_5$S | found |
|---|---|---|
| % C: | 52.52 | 52.46 |
| % H: | 5.09 | 5.08 |
| % N: | 4.71 | 4.79 |
| % S: | 10.78 | 10.57 |

IR spectrum (cm$^{-1}$): 1190 and 1388 —SO$_2$—O—; 1782 carbonyl.

EXAMPLE 5

Allylbicyclo[2.2.1]hept-5-ene-2,3-dicarboxylic acid N-(2',2'-dimethyl-3'-methanesulfonyloxypropyl)imide

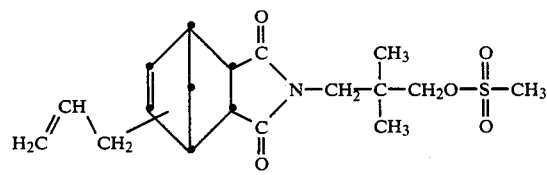

(a)

Allylbicyclo[2.2.1]hept-5-ene-2,3-dicarboxylic acid N-(2',2'-dimethyl-3'-hydroxypropyl)imide 204 g of allylbicyclo[2.2.1]hept-5-ene-2,3-dicarboxylic acid anhydride are reacted with 103 g of neopentanolamine for 4 hours at 120° C., and the product is isolated by distillation. 268 g (92.7% of theory) of a yellow oil with a refractive index $n_{25}^D$ of 1.5190 and a viscosity of 6.21 Pa.s are obtained at a temperature in the range from 169° to 172° C. at 2.53 Pa.

| Analysis: | calc. | found |
|---|---|---|
| % C: | 70.56 | 70.67 |
| % H: | 8.01 | 8.13 |
| % N: | 4.84 | 4.77 |
| % OH: | 5.88 | 5.69 |

The hydroxyl group content is determined by acetylation with acetanhydride in pyridine.

(b)

72.25 g of the product prepared according to (a)
27.32 g of the triethylamine
250 g of toluene and
28.64 g of methanesulfonyl chloride are reacted according to the procedure described in Example 1b, affording 81.75 g (89.1% of theory) of a brown clear resin, $\eta_{80} = 0.414$ Pa.s.

| Elementary analysis: | calc. for $C_{18}H_{25}NO_5S$ | found |
|---|---|---|
| % C: | 58.84 | 59.89 |
| % H: | 6.86 | 6.99 |
| % N: | 3.81 | 3.77 |
| % S: | 8.72 | 8.02 |

| Elementary analysis: | calc. for $C_{23}H_{27}NO_6S$ | found |
|---|---|---|
| % C: | 62.01 | 62.01 |
| % H: | 6.11 | 6.17 |
| % N: | 3.14 | 3.06 |
| % S: | 7.20 | 6.80 |

EXAMPLE 7

Allylbicyclo[2.2.1]hept-5-ene-2,3-dicarboxylic acid N-[2'-(2''-napthalenesulfonyloxy)ethyl]imide

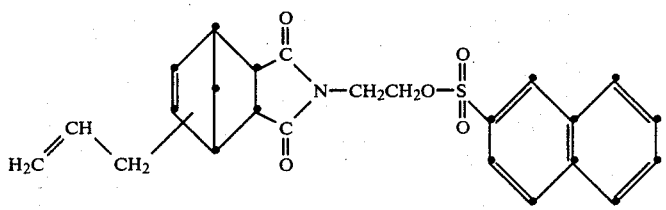

EXAMPLE 6

Allylbicyclo[2.2.1]hept-5-ene-2,3-dicarboxylic acid N-[(2'-(2''-p-toluenesulfonyloxyethoxy)ethyl]imide

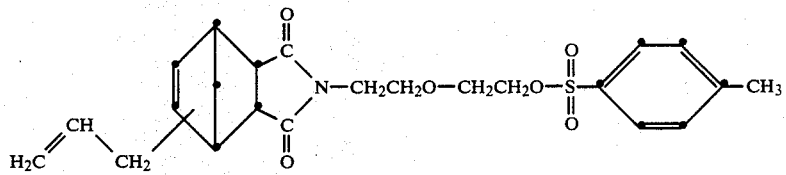

(a)

Allylbicyclo[2.2.1]hept-5-ene-2,3-dicarboxylic acid N-[2'-(2''-hydroxyethoxy)ethyl]imide 120 g of allylbicyclo[2.2.1]hept-5-ene-2,3-dicarboxylic acid anhydride are reacted with 67.9 g of diglycolamine at 140° C., the reaction mixture is heated to 200° C. and the pressure is lowered to 10.6 Pa, affording 142.6 g of a yellow oil with a viscosity of 1.55 Pa.s at 25° C. and an $n_{25}^D$ of 1.5230.

| Analysis: | calc. | found |
|---|---|---|
| % C: | 65.96 | 65.74 |
| % H: | 7.27 | 7.39 |
| % N: | 4.81 | 4.71 |
| % OH: | 5.84 | 5.34 |

(b)

72.75 g of the product prepared according to (a)
27.9 g of triethylamine
250 g of toluene and
47.6 g of p-toluenesulfonyl chloride
are reacted according to the procedure described in Example 1b, affording 93.1 g (83.7% of theory) of a reddish brown liquid resin with a viscosity of 3.1 Pa.s at 40° C.

With vigorous stirring, 90.67 g of finely pulverised napthalene 2-sulfochloride are dispersed in a solution of 98.8 g of hydroxyethylimide, perpared according to Example 3a, and 44.52 g of triethylamine in 500 g of toluene at a temperature in the range from 0° to 5° C. The reaction mixture is allowed to warm to room temperature, is then stirred for several hours and subsequently neutralised with 1N HCl. The mixture is washed with three 250 ml portions of $H_2O$, dried over 30 g $Na_2SO_4$ and filtered. The toluene is distilled off by rotary evaporation (130° C./15 mm Hg), affording 150.8 g (81.8% of theory) of a brown liquid which on cooling congeals to a wax-like mass which melts between 66° and 74° C.

| Elementary analysis: | calc. for $C_{24}H_{23}NO_5S$ | found |
|---|---|---|
| % C: | 65.90 | 65.51 |
| % H: | 5.26 | 5.40 |
| % N: | 3.20 | 3.28 |
| % H: | 7.32 | 7.08 |

EXAMPLE 8

Allylbicyclo[2.2.1]hept-5-ene-2,3-dicarboxylic acid N-(4'-methanesulfonyloxyphenyl)imide

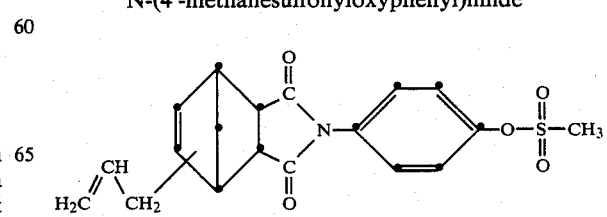

(a)

Allylbicyclo[2.2.1]hept-5-ene-2,3-dicarboxylic acid N-(4'-hydroxyphenyl)imide

A solution of 101 g of allylbicylo[2.2.1]hept-5-ene-2,3-dicarboxylic acid anhydride and 54.5 g of 4-aminophenol in 155 g of toluene is heated to boiling point, and the water formed during imidation is separated in a Hahn stillhead.

(b)

This solution is diluted with a further 350 g of toluene, 55.6 g of triethylamine are added and the mixture is cooled to 0° C. With stirring, 57.05 g of methane sulfochloride are added dropwise, while holding the temperature in the range from 5° to 8° C. by external cooling. The mixture is then stirred overnight at room temperature. The pH is adjusted with 1N HCl to 5.5 and the mixture is then washed with water and dried. The product is isolated as described in EXAMPLE 7. Yield: 162 g (86.86% of theory).

| Elementary analysis: | calc. for $C_{19}H_{19}NO_5S$ | found |
|---|---|---|
| % C: | 61.11 | 61.66 |
| % H: | 5.13 | 5.24 |
| % N: | 3.75 | 3.70 |
| % S: | 8.59 | 8.37 |
| molecular weight | 373.4 | 381 |

EXAMPLE 9

Allylbicyclo[2.2.1]hept-5-ene-2,3-dicarboxylic acid N-(2'-methanesulfonyloxyethyl)imide 49.26 g of allylbicyclo[2.2.1]hept-5-ene-2,3-dicarboxylic acid N-(2'-hydroxyethyl)imide (prepared according to Example 3a) and 22.26 g of triethylamine are dissolved in 160 g of toluene, and the solution is cooled under nitrogen to 5° C. With stirring, 22.91 g of methane sulfochloride are added dropwise for 1 hour, while keeping the temperature in the range from 5° to 10° C. by external cooling. The mixture is subsequently stirred for a further 18 hours at room temperature. The pH is adjusted with 1N HCl to 5 and the mixture is washed with water and dried. The product is isolated as described in Example 7. Yield: 54 g (83.0% of theory); $\eta_{40°\ C.}=2138.4$ mPa.s; $n_{25}^D=1.5238$.

| Elementary analysis: | calc. for $C_{15}H_{19}NO_5S$ | found |
|---|---|---|
| % C: | 55.37 | 55.71 |
| % H: | 5.89 | 6.00 |
| % N: | 4.30 | 4.28 |
| % S: | 9.85 | 9.47 |

APPLICATION EXAMPLES

The resins A and B indicated below are cured in the presence of N-sulfonyloxyimides of the present invention which act as latent catalysts.

RESIN A

N,N'-Hexamethylene-bis(allylbicyclo[2.2.1]hept-5-ene-2,3-dicarboxylic acid imide, prepared according to Example 9 of European patent application No. 0 105 024.

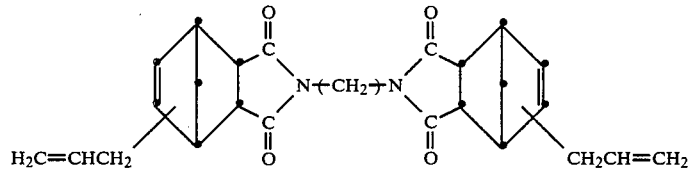

RESIN B

Bis[4-(allylbicyclo[2.2.1]hept-5-ene-2,3-dicarboxylic acid imidophenyl)methane], prepared according to Example 11 of European patent application No. 0 105 024.

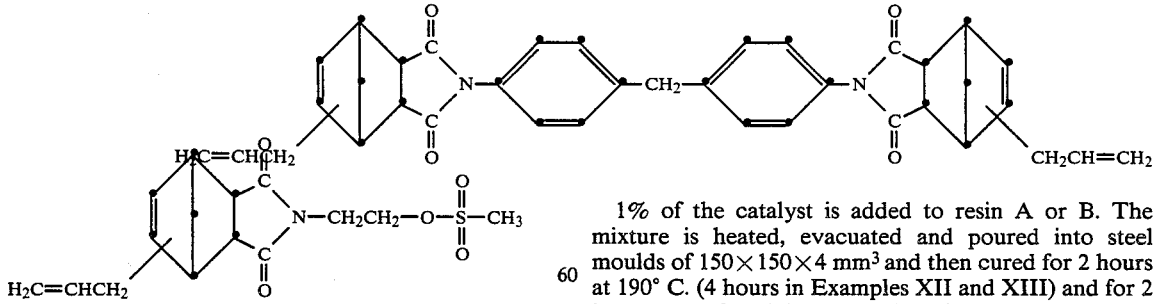

1% of the catalyst is added to resin A or B. The mixture is heated, evacuated and poured into steel moulds of 150×150×4 mm³ and then cured for 2 hours at 190° C. (4 hours in Examples XII and XIII) and for 2 hours at 250° C. The properties of the cured products are indicated in Table 1.

TABLE 1

| Application Example No. | Resin | Catalyst acc. to Example No. | Flexural strength (DIN 53452) | Edge fibre elongation % (DIN 53452) | Impact flexural strength (DIN 53453) | $T_G$* °C. |
|---|---|---|---|---|---|---|
| I | A | 1 | 112.2 | 4.3 | 11.3 | 196 |

TABLE 1-continued

| Application Example No. | Resin | Catalyst acc. to Example No. | Flexural strength (DIN 53452) | Edge fibre elongation % (DIN 53452) | Impact flexural strength (DIN 53453) | $T_G$* °C. |
|---|---|---|---|---|---|---|
| II | B | 1 | 99.0 | 3.4 | 6.1 | 280 |
| III | A | 2 | 95.6 | 3.4 | 11.4 | 193 |
| IV | B | 2 | 20.5 | 0.6 | 0.9 | 275 |
| V | B | 3 | 52.8 | 1.7 | 3.2 | 289 |
| VI | A | 4 | 117.6 | 5.2 | 16.4 | 251 |
| VII | B | 4 | 82.5 | 2.8 | 6.6 | 266 |
| VIII | B | 5 | 80.0 | 2.8 | 7.5 | 302 |
| IX | A | 6 | 111.1 | 4.4 | 10.5 | 186 |
| X | B | 6 | 60.1 | 2.0 | 2.9 | 289 |
| XI | A | 7 | 104.0 | 4.3 | 13.4 | 195 |
| XII | B | 8 | 65.7 | 2.0 | 4.7 | 281 |
| XIII | B | 9 | 88.7 | 2.9 | 7.9 | 300 |

*Determined with a thermoanalyser TA 2000 of the company METTLER (Greifensee, Switzerland)

What is claimed is:

1. An imide of formula I

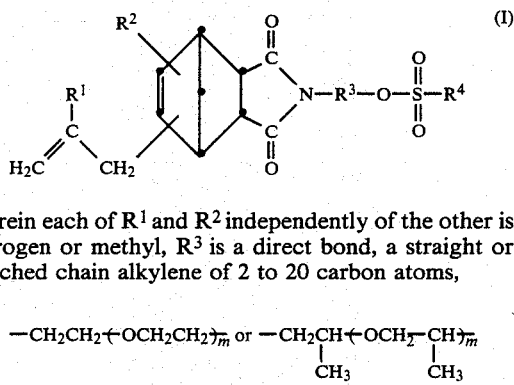

wherein each of $R^1$ and $R^2$ independently of the other is hydrogen or methyl, $R^3$ is a direct bond, a straight or branched chain alkylene of 2 to 20 carbon atoms,

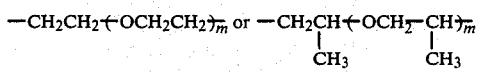

where m is 1 to 8, cycloalkylene of 5 to 8 carbon atoms, bi-(cyclohexylene)methane, 2,2-bis-(cyclohexylene)-propane, decahydronaphthylene, phenylene, naphthylene, said phenylene or said naphthylene substituted by one or more $C_1$–$C_4$-alkyl groups, or a group of the formula II

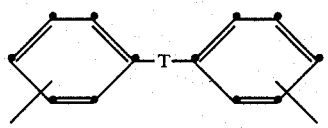

wherein T is methylene, isopropylidene, CO, O, S or $SO_2$, and $R^4$ is $C_1$–$C_{12}$alkyl, $C_5$–$C_8$cycloalkyl, $C_6$–$C_{10}$ aryl, benzyl or $C_7$–$C_{12}$-alkaryl.

2. An imide of formula I according to claim 1, wherein $R^3$ is a direct bond, an alkylene of 2 to 10 carbon atoms, a —$CH_2CH_2$—$(OCH_2CH_2)$—$_m$ where m is 1 or 2, cycloalkyene of 5 to 6 carbon atoms, phenylene, naphthylene or said phenylene substituted by $C_1$–$C_4$ alkyl, or a group of formula II wherein T is methylene or isopropylidene.

3. An imide of formula I according to claim 1, wherein each of $R^1$ and $R^2$ is hydrogen.

4. An imide of formula I according to claim 1, wherein $R^4$ is $C_1$–$C_6$alkyl, $C_5$–$C_6$cycloalkyl, $C_6$–$C_{10}$aryl or $C_7$–$C_{12}$alkaryl.

5. An imide of formula I according to claim 1, wherein $R^3$ is a direct bond or the radical —$CH_2CH_2$—,

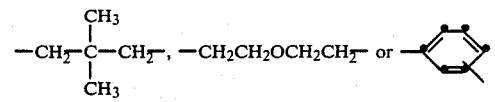

$R^4$ is methyl, phenyl, 2-naphthyl or p-tolyl.

6. An imide of formula I according to claim 1, wherein each of $R^1$ and $R^2$ is hydrogen, $R^3$ is a direct bond or the radical —$CH_2CH_2$— and $R^4$ is methyl or phenyl.

7. An imide of formula I according to claim 1, wherein each of $R^1$ and $R^2$ is hydrogen, $R^3$ is a direct bond and $R^4$ is phenyl.

8. An imide of formula I according to claim 1, wherein each of $R^1$ and $R^2$ is hydrogen, $R^3$ is a direct bond and $R^4$ is methyl.

9. An imide of formula I according to claim 1, wherein each of $R^1$ and $R^2$ is hydrogen, $R^3$ is the radical —$CH_2CH_2$— and $R^4$ is methyl.

* * * * *